United States Patent [19]

Timar et al.

[11] Patent Number: 5,223,629
[45] Date of Patent: Jun. 29, 1993

[54] PROCESS FOR THE PREPARATION OF ANTI-HYPERTENSIVE BENZOPYRAN

[75] Inventors: Tibor Timar; Tibor Eszenyi; Peter Sebok; Vilmos Galamb; Julia Fazekas; Terezia Istvan; Eva Kovach, all of Tiszavasvari; Erika Nagy, Tiszalok, all of Hungary

[73] Assignee: Alkaloida Vegyeszeti Gyar, Tiszavasvari, Hungary

[21] Appl. No.: 809,714

[22] Filed: Dec. 17, 1991

Related U.S. Application Data

[63] Continuation-in-part of Ser. No. 543,142, Jun. 25, 1990, Pat. No. 5,145,985.

[30] Foreign Application Priority Data

Jul. 21, 1989 [HU] Hungary ............................ 3699/89

[51] Int. Cl.⁵ .................. C07D 405/04; C07D 311/72
[52] U.S. Cl. .................................... 548/525; 549/400; 549/401
[58] Field of Search ................ 548/525; 549/400, 401

[56] References Cited

U.S. PATENT DOCUMENTS

| 4,214,963 | 7/1980 | Blanco | 204/158 R |
| 4,446,113 | 5/1984 | Evans | 549/399 |
| 5,013,853 | 5/1991 | Gericke et al. | 549/401 |

FOREIGN PATENT DOCUMENTS

| 118794A | 9/1984 | European Pat. Off. | 549/389 |
| 3820506 | 12/1989 | Fed. Rep. of Germany . | |
| 2204868 | 11/1988 | United Kingdom . | |

OTHER PUBLICATIONS

Bolzoni et al. "selective in reactions . . . " Angew. Chem. Int. Ed. English 17 (1978) 684–686.

Bergmann et al. "Synthesis . . . " J. Med. Chem. 33 (2) 492–504 (1990).

Nebergall et al. "College Chemi . . . " Heath and Co. pp. 324–325 (1968).

Primary Examiner—C. Warren Ivy
Assistant Examiner—Celia Chang
Attorney, Agent, or Firm—Herbert Dubno; Jonathan Myers

[57] ABSTRACT

A process is disclosed for the preparation of (±)-6-cyano-3,4-dihydro-2,2-dimethyl-trans-4-(2-oxo-1-pyrrolidino)-2H-1-benzopyran-3-ol of the Formula (VI)

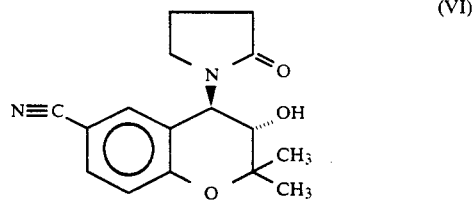

from 4-cyanophenol of the Formula (I)

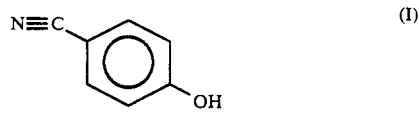

which comprises reacting 4-cyanophenol of the Formula (I) with isoprene, followed with bromination and dehydrobromination steps with formation of intermediates to react with 2-pyrrolidone resulting in obtaining the compound of the Formula (VI).

7 Claims, No Drawings

PROCESS FOR THE PREPARATION OF ANTI-HYPERTENSIVE BENZOPYRAN

CROSS REFERENCE TO RELATED APPLICATION

This application is a continuation-in-part of Ser. No. 07/543,142 filed Jun. 25, 1990, now U.S. Pat. No. 5,145,985 issued Sep. 8, 1992.

FIELD OF THE INVENTION

The present invention is directed to a new process for the preparation of (+)-6-cyano-3,4-dihydro-2,2-dimethyl-trans-4-(2-oxo-1-pyrrolidinyl)-2H-1-benzopyran-3-ol of the formula (VI)

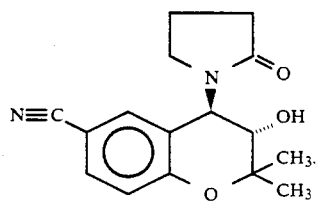

known as Kromakalim (BRL-34 915).

BACKGROUND OF THE INVENTION

Kromakalim is an anti-hypertensive composition of novel acting mechanism. It belongs to the peripheral group of anti-hypertensive agents, it acts by opening the potassium channels in the smooth muscle cells and it thereby prevents the accumulation of electric potential through the membranes. Accordingly it belongs to the potassium channel activators [Drugs of the Future II, 175 (1986), 12, 284 (1987), 13, 269 (1988), 14, 276 (1989)].

Several independent methods are known for the preparation of Kromakalim and analogues thereof: J. M. Evans et al.: J. Med. Chem. 26, 1582 (1983), J. M. Evans et al.: J. Med. Chem. 27, 1127 (1984), V. A. Ashwood et al.:J. Med. Chem. 29, 2194 (1986), EPO 0 009 912, EPO 0 046 652, EPO 0 076 075, EPO 0 093 535, EPO 0 120 426, EPO 0 120 427, EPO 0 120 428, EPO 0 126 311, EPO 0 126 350, EPO 0 126 367, EPO 0 138 134, EPO 0 173 848, EPO 0 271 271, EPO 0 274 821, EPO 0 277 611, EPO 0 286 975, PCT WO 85 00602, PCT WO 85 01290, PCT WO 88 00822.

According to EPO 0 076 075 describing the possibilities for preparing Kromakalim 4-cyano-phenol of the formula (I)

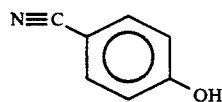

is reacted with 3-chloro-3-methyl-butyne resulting in propargyl-ether of the formula (IX)

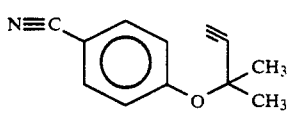

which is then subjected to ring closure to produce 6-cyano-2,2-dimethyl-2H-1-benzopyran of the formula (III)

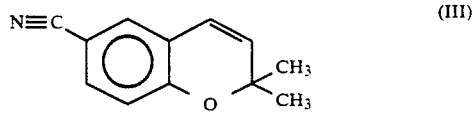

The compound of the formula (III) is then converted through 6-cyano-trans-3-bromo-3,4-dihydro-2,2-dimethyl-2H-1-benzopyran-4-ol to 6-cyano-3,4-dihydro-3,4-epoxy-2,2-dimethyl-2H-1-benzopyran of the formula (V).

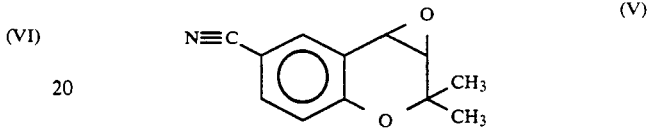

From the compound of the formula (V) the end-product of the formula (VI) can be obtained by three independent routes.

1. The compound of the Formula (V) is reacted with ammonia to produce 6-cyano-3,4-dihydro-2,2-dimethyl-trans-4-amino-2H-1-benzopyran-3-ol of the formula (VII)

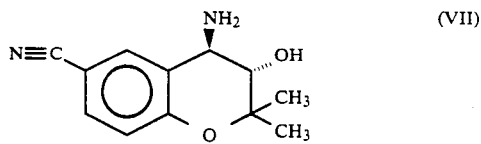

which is then reacted with 4-chloro-butyric acid chloride to produce a compound of the formula (VIII)

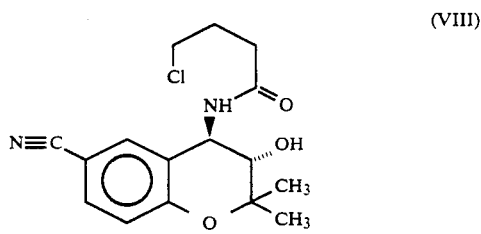

and this is then subjected to ring closure in a sodium-hydride-tetrahydrofuran system.

2. The compound of the formula (V) is reacted with 4-amino-butyric acid in a sodium-hydrogen-carbonate-ethanol system, and the ring closure results in the end-product of the formula (VI).

3. The compound of the formula (V) is reacted with 2-pyrrolidone in the presence of sodium hydride and dimethylsulfoxide and the end-product of the formula (VI) is obtained.

When reproducing the working examples of EPO 0 076 075 we observed the following circumstances:

4-cyano-phenol reacts with 3-chloro-3-methyl-butyne in the presence of sodium hydroxide-benzyl-trimethyl-ammonium-hydroxide-water and dichlorobutane at room temperature within 5–6 days, according to the patent specification propargyl-ether of the formula (IX) can be obtained with a yield of 69%. The reaction was repeated several times but only a 46-50% yield could be achieved. The reaction was carried out in acetone, dimethyl-sulfoxide, N,N-dimethyl-formamide solvent in the presence of potassium-carbonate and potassium-iodide at 50°-150° C., and after 30-40 hours reaction only 40-55% yield could be achieved. The further problem is that only 3-hydroxy-3-methyl-butyne is commercially available and according to our experiences 3-chloro-3-methyl-butyne can be prepared from this compound with a yield of only 55-60% by a difficult reaction. 3-chloro-3-methyl-butyne is a compound of poor stability; it decomposes upon standing and at the same time it polymerizes during the alkylation reaction or it decomposes at higher temperature. It can be said that the reaction of 4-cyano-phenol of the formula (I) and 3-chloro-3-methyl-butyne results in propargyl-ether of the formula (IX) with a yield of only 45-55%, and this is then subjected to ring-closure in ortho-dichloro-benzene to 6-cyano-2,2-dimethyl-2H-1-benzopyran of the formula (III) with a yield of 80% according to EPO 0 076 075. According to our own experimental experience the reaction can be carried out with a yield of at most 70% and the purification of the product of the formula (III) is a complicated procedure and can be performed by vacuum distillation or column chromatography. By this reaction the chromene derivatives of the formula (III) can be obtained with a yield of 35% related to 4-cyano-phenol of the formula (I) and with a yield of 23% related to 3-chloro-3-methyl-butyne.

3-bromo-4-hydroxy-derivatives of the formula (IV)

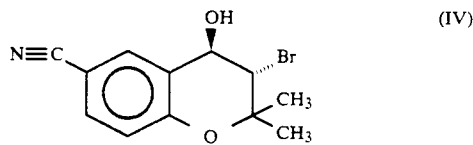

could be prepared from the chromene of the formula (III) in a system of dimethyl-sulfoxide and water with a yield of 90% according to EPO 0 076 075. Similarly, epoxide of the formula (V) could be obtained by a yield of 90% by reacting 3-bromo-4-hydroxy-derivative of the formula (IV) with sodium-hydroxide in the presence of a solvent mixture of dioxane and water that is the conversion of (III)→(IV)→(V) could be reproduced.

The preparation of the end-product of the formula (VI) was carried out by a way which seemed to be the most simple method, that is epoxide of the formula (V) was reacted with 3-pyrrolidone in the presence of sodium-hydride and dimethyl-sulfoxide. As to our surprise a rather complex reaction mixture was obtained and by thin layer chromatography 6-8 components could be detected the amount of which was commeasurable. The reaction was repeated several times, and the end-product of the formula (VI) could be prepared with a yield of 20-25% only by the complicated column chromatography as opposed to the yield of 60% in the disclosure.

According to the procedure disclosed in the EPO 0 076 075 the end-product of the formula (VI) could be prepared only by a yield of 22-26% related to 4-cyano-phenol of the formula (I) and the procedure when reproduced by our own experiments could be carried out with a yield of only 6-8%.

Accordingly, the procedures disclosed in EPO 0 076 075 are not suitable for the industrial preparation of Kromakalim of the formula (VI).

OBJECT OF THE INVENTION

The object of the invention is to elaborate a new economic and industrially available process for the preparation of Kromakalim of the formula (VI).

SUMMARY OF THE INVENTION

The present invention is directed to a new process for the preparation of (±)-6-cyano-3,4-dihydro-2,2-dimethyl-trans-4-(2-oxo-1-pyrrolidinyl)-2H-1-benzopyran-3-ol of the formula (VI) starting from 4-cyano-phenol of the formula (I) comprising reacting 4-cyano-phenol of the formula (I) with isoprene resulting in 6-cyano-2,2-dimethyl-3,4-dihydro-2H-1-benzopyran of the formula (II)

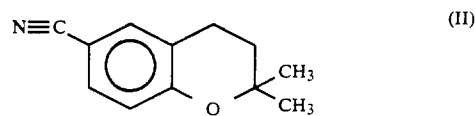

which is then converted to 6-cyano-2,2-dimethyl-2H-benzopyran of the formula (III) which is either converted to epoxide of the formula (V) in one step and converting the epoxide of the formula (V) to the end-product of the formula (VI) or compound of the formula (III) is converted to 3-bromo-4-hydroxy-derivative of the formula (IV) which is then in one step converted to the end-product of the formula (VI).

The most important basis of our invention is that we have recognized that by reacting 4-cyano-phenol of the formula (I) with isopropene under mild reaction conditions the new compound of the formula (II) 6-cyano-3,4-dihydro-2,2-dimethyl-2-H-1-benzopyran is obtained by an excellent yield. It is known that the reactions of substituted phenols and isoprene in the presence of alkali metals, preferably potassium and Lewis-acids, preferably aluminium-trichloride in aromatic solvents, preferably benzene at 60°-100° C. result within 6-10 hours in substituted 3,4-dihydro-2,2-dimethyl-2H-1-benzopyrans with a yield of 80-90% [L. Bolzoni et al.: Angew. Chem. Int. Ed. Engl. 17, 684 (1978)]. Other Lewis-acids specifically disclosed by Bolzoni et al include SnCl₄ and FeCl₃. According to Japanese patent specifications 40 637/80, 43 039/80 and 15411/80 by reacting alkoxy-phenols and isoprene in an acid catalyzed reaction similarly quantitatively alkoxy-3,4-dihydro-2,2-dimethyl-2H-1-benzopyrans can be obtained. As an acid, hydrochloric acid, sulphuric acid, ortho-phosphoric acid, perchloric acid, methanesulfonic acid, para toluene-sulfonic acid can be used, and as a solvent water inmiscible organic solvents, such as hexane, benzene, toluene and chloroform, carbon tetrachloride are suitable, and the reaction can be carried out at 30°-120° C. within 5-15 hours. According to our experiments when reacting 4-cyano-phenol of the formula (I) with isoprene under the mentioned reaction conditions 6-cyano-3,4-dihydro-2,2-dimethyl-2H-1-benzopyran of the formula (II) was obtained with a yield of 90-95% which is according to our knowledge a new compound. The conversion of the compound of the formula (II) to 6-cyano-2,2-dimethyl-2H-1-benzopyran of the formula (III) can be performed by several independent routes:

1) The compound of the formula (II) is brominated in the benzyl position by N-bromo-succinimide in haloalkanes in the presence of a trace of peroxide and 6-cyano-3,4-dihydro-2,2-dimethyl-4-bromo-2H-1-benzopyran of the formula (X)

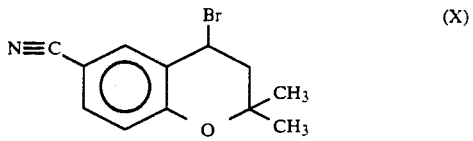

is almost quantitatively formed and this can be similarly with almost quantitative yield dehydrobrominated with alkali alcoholates to produce 6-cyano-2,2-dimethyl-2H-1-benzopyran of the formula (III).

2) The new compound of the formula (II) can be oxidized in one step with an almost quantitative yield by using lead tetraacetate in glacial acetic acid or with DDQ in an apolar solvent.

A further basic point of our invention is that we can epoxidate the compound of the formula (III) in one step to the derivative of the formula (V) by using peracides in the presence of a haloalkane type solvent: M. Bartók and K. L. Láng. Oxiranes, Chapter 14, 610–618., in: The Chemistry of Functional Groups (Ed. by S. Patai), Supplement E. Part 2, Intersci. Publ. John Wiley and Sons (1980).

The end-product of the formula (VI) can be prepared from the epoxide of the formula (V) in the presence of an alkali metal, preferably sodium or alkali metal-alcoholate preferably potassium-tert-butylate by reacting it with 2-pyrrolidone serving also as a solvent at 25°–70° C. within 5–8 hours with a yield of 90%.

If a 3-bromo-4-hydroxy-derivative of the formula (IV) is prepared from the compound of the formula (III) with N-bromo-succinimide than the reaction is preferably carried out in a solvent mixture of tetrahydrofuran or 1,4-dioxane with water. We have further recognized that when reacting a 3-bromo-4-hydroxy-derivative of the formula (IV) with 2-pyrrolidone serving also as a solvent in the presence of alkali-metal-alcoholate, preferably potassium-tert-butylate at 25°–70° C., then the end-product of the formula (VI) can be obtained within 8–12 hours with an almost quantitative yield.

Summarizing, our present invention is directed to a new process for the preparation of (±)-6-cyano-3,4-dihydro-2,2-dimethyl-trans-4-(2-oxo-1-pyrrolidinyl)-2H-1-benzopyran-3-ol of the formula (VI) from 4-cyano-phenol of the formula (I) by reacting 4-cyano-phenol of the formula (I) with isoprene at 30°–120° C. in a solvent in the presence of alkali-metals and/or catalysts resulting in 6-cyano-3,4-dihydro-2,2-dimethyl-2H-1-benzopyran of the formula (II) which is then converted to 6-cyano-2,2-dimethyl-2H-1-benzopyran of the formula (III) at 40°–150° C. in a solvent by using a catalyst and/or an oxidizing agent or by bromination in the benzyl position and by dehydrobromination of the compound of the formula (X), and a) preparing 6-cyano-3,4-dihydro-2,2-dimethyl-3,4-epoxy-2H-1-benzopyran of the formula (V) in one step at 0°–20° C. by using a peracid in a solvent and converting the obtained compound of the formula (V) to the end-product of the formula (VI) by reacting it with 2-pyrrolidone in the presence of alkali-metals or alkali-metal-alcoholates at 20°–100° C., b) reacting a compound of the formula (III) with N-bromo-succinimide in a solvent at 20°–100° C. to produce 6-cyano-3,4-dihydro-2,2-dimethyl-trans-3-bromo-4-hydroxy-2H-1-benzopyran of the formula (IV) which is then reacted with 2-pyrrolidone in the presence of alkali metals or alkali-metals-alcoholates at 20°–100° C. to result in the end-product of the formula (VI). Our present invention has the following advantages:

- 4-cyano-phenol of the formula (I) reacts unambiguously with isoprene with an almost quantitative yield,
- isoprene is an inexpensive, easily available industrial intermediate product,
- chromene of the formula (III) can be obtained with unambiguous reactions with a good yield, and thereby purified by crystallization (as opposed to the vacuum distillation disclosed in EPO 0 076 075),
- epoxide of the formula (V) can be obtained according to our invention in high purity in a crystalline form,
- end-product of the formula (VI) can be obtained under mild reaction conditions (there is no need to use the expensive sodium-hydride and dimethyl-sulfoxide which is dangerous for the environment and which can only be handled with difficulty,
- the purification of the product and the working up of the reaction mixture is simple,
- the solvents used can be recovered by distillation and can be recycled,
- the reaction can be easily handled and their size can be increased,
- industrial production does not need special equipment and the reactions can be carried out in conventional industrial equipment.

According to the new process Kromakalin can be obtained with a yield of 55–65% related to 4-cyano-phenol of the formula (I) as opposed to the maximal 6–8% yield disclosed in EPO 0 076 075 and reproduced by our experiments.

Our present invention is further illustrated with the following examples.

EXAMPLE 1

Preparation of the compound of the Formula (II)

11.9 g (0.1 moles) of 4-cyano-phenol are dissolved in 200 ml of absolute benzene and 1.95 g (0.05 moles) of potassium metal are added in small portions under a nitrogen atmosphere. The mixture is stirred until evolution of hydrogen. When the evolution of hydrogen gas has ceased, 13.3 g (0.1 moles) of aluminum trichloride are added under stirring. 10 ml (0.1 moles) of isoprene and 50 ml of absolute benzene are added dropwise. The reaction mixture is boiled for 6 hours. The reaction mixture is cooled and a solution of 250 ml saturated ammonium-chloride is added. The layers are separated, the organic layer is washed to neutral, dried above sodium-sulphate and the solvent is removed in vacuo. 17.29 g (92%) of colourless oil are obtained.

$n_D^{24}$: 1.5475.

| Analysis: | C | H | N |
|---|---|---|---|
| calculated (%) | 76.98 | 6.99 | 7.48 |
| found (%) | 76.80 | 7.07 | 7.40 |

PMR (CDCl$_3$): 1.35 (6H, s, 2CH$_3$), 1.83 (2H, t, J=7 Hz, 3—CH$_2$), 2.80 (2H, t, J=7 Hz, 4—CH$_2$), 6.80 (1H, dd, J$_1$=8 Hz, J$_2$=1 Hz, 7—H), 7.34 (2H, m, 5H, and 8H)

MS (EI): 187 (60%, M+), 172 (79%), 158 (32%), 144 (12%), 132 (100%), 116 (15%).

EXAMPLE 2

Preparation of the compound of the formula (X)

19.7 g (0.1 mole) of the compound of the formula (II) are dissolved in 200 ml of carbon-tetrachloride and 18.7 g (0.105 mole) N-bromo-succinimide and 1 g of dibenzoyl-peroxide are added.

The reaction mixture is boiled for 5 hours. It is cooled, and the precipitated succinimide is filtered, washed with 2×200 ml of carbon-tetrachloride and the combined organic layer is washed to neutral and dried above sodium-sulphate and the solvent is removed. 25 g (94%) of crystalline substance are obtained.

Mp.: 78°–79° C.

| Analysis: | C | H | Br | N |
|---|---|---|---|---|
| calculated (%) | 56.16 | 4.54 | 30.02 | 5.26 |
| found (%) | 56.00 | 4.60 | 30.10 | 5.20 |

PMR (DMSO-$d_6$): 1.29 (3H, s, $CH_3$), 1.47 (3H, s, $CH_3$), 2.26–2.69 (2H, m, 3—$CH_2$), 5.76 (1H, m, Br—CH), 6.93 (1H, d, J=10 Hz, 8—H), 7.64 (1H, dd, $J_1$=10 $J_2$=2 Hz, 7—H), 7.90 (1H, d, J=2 Hz, 5—H).

EXAMPLE 3

Preparation of the compound of the formula (III)

26.6 g (0.1 mole) of the compound of the formula (X) are dissolved in 300 ml of benzene and 11.2 g (0.1 mole) of potassium-tert-butylate are added. The reaction mixture is boiled for 4 hours. It is cooled and washed with 3×200 ml of water and dried above sodium-sulphate. After evaporation 17.5 g (95%) of crystalline substance are obtained.

Mp.: 45°–47° C.

IR (KBr): 2230 $cm^{-1}$ (literature melting point: 36°–37° C. (M. Harfenist and E. Thom: J. Org. Chem. 841 (1972)).

EXAMPLE 4

Preparation of the compound of the formula (III)

26.6 g (0.1 mole) of the compound of the formula (X) are dissolved in 250 ml of benzene and 75.5 g (0.1 mole) 90% sodium-ethylate are added and the reaction mixture is boiled for 6 hours. The following procedure is analogous to example 3. 17 g (92%) of solid substance are obtained, melting at 45°–46° C.

EXAMPLE 5

Preparation of the compound of the formula (II)

11.9 g (0.1 mol) of 4-cyano-phenol are added to a stirred mixture of 220 g of 48% sulfuric acid solution and 200 g of chloroform. At room temperature 14 g (0.2 mole) of isoprene are added and the reaction mixture is vigorously stirred at 60° C. for 5 hours. The mixture is cooled, the layers are separated and the organic layer is washed with 2×100 ml of water, 2×150 ml of 5% sodium hydrogen carbonate solution and 2×100 ml water, and the mixture is then dried above sodium sulphate. The solvent is removed in vacuo. 17.7 g (95%) of colourless oil are obtained the physical constant and spectral data of which are identical with the data disclosed in example 1.

EXAMPLE 6

Preparation of the compound of the formula (II)

11.9 g (0.1 mole) 4-cyano-phenol are added to a stirred mixture of 25 g of 85% ortho-phosphoric acid solution and 250 g of chloroform. At room temperature 10.5 g (0.15 mole) isoprene are added, and the mixture is vigorously stirred at 60° C. for 4 hours. One may further proceed as disclosed in example 5. 17.5 g (93%) of colourless oil are obtained.

EXAMPLE 7

Preparation of the compound of the formula (II)

11.9 g (0.1 mole) of 4-cyano-phenol are added to a stirred mixture of 40 g of 30% hydrochloric-acid solution and 200 g of chloroform. 21 g (0.3 mole) isoprene are added at room temperature and the mixture is vigorously stirred at 60° C. for 5 hours. One may further proceed as disclosed in example 5. 16.8 g (90%) of colourless oil are obtained.

EXAMPLE 8

Preparation of the compound of the formula (III)

18.7 g (0.1 mole) of the compound of the formula (II), 22.7 g (0.1 mole) 2,3-dichloro-5,6-dicyano-1,4-benzoquinone are boiled in 300 ml of absolute benzene for 38 hours. The solution is cooled, filtered and the mother lye is washed with 3×100 ml of 5% sodium hydrogen carbonate, 3×100 ml of water and dried above sodium sulphate and the solvent is removed. 17 g (92%) crystalline substance are obtained, melting at 45°–47° C.

EXAMPLE 9

Preparation of the compound of the formula (III)

18.7 g (0.01 mole) of the formula (II) are boiled for 2 hours in 150 ml of glacial acetic acid in the presence of 41.5 g lead tetraacetate. The mixture is cooled and poured on 200 g of crushed ice, extracted with 3×100 ml of chloroform and the organic layer is washed with 3×100 ml 5% sodium-hydrogen carbonate and with 3×100 ml of water. The mixture is dried above sodium sulphate and after removing the solvent 17.4 g, 94% of solid substance are obtained melting at 46°–47° C.

EXAMPLE 10

Preparation of the compound of the formula (V)

18.5 g (0.1 mole) of the compound of the formula (III) are dissolved in 300 ml of chloroform at room temperature whereafter the solvent is cooled with ice to 0–5% and 37.74 g (0.011 mole) 50% meta-chloro-perbenzoic acid are added. The mixture is further stirred for 3 hours and after ceasing the cooling the reaction is continued for 20 hours. The chloroform layer is then washed with 5% sodium hydroxide solution and water. The organic layer is dried above sodium-sulphate and evaporated. Upon cooling a yellow slowly crystallizing oil is obtained.

Yield: 19.10 g (95%)

Mp.: 104°–105° C. (literature: gum, [J. M. Evans et al.: J. Med. Chem. 26, 1582 (1983)].

EXAMPLE 11

Preparation of the compound of the formula (V)

12.50 g (0.15 mole) sodium-hydrogen-carbonate are dissolved in 200 ml of water and the solution is then vigorously stirred with a solution of 18.52 g (0.1 mole) of the compound of the formula (III) in 300 ml chloroform. The reaction mixture is cooled to 0°–5° C. and 37.74 g (0.11 mole) 50% meta-chloro perbenzoic acid are added. The mixture is further stirred for 3 hours and then after stopping the cooling the reaction is continued for 20 hours. The layers are separated, the chloroform layer is washed with a 5% sodium-hydroxide solution and with water. The organic layer is dried above sodium-sulphate and evaporated. Upon standing a pale yellow slowly crystallizing substance is obtained.

Yield: 18.50 g (92%).
Mp.: 103°–104° C.

EXAMPLE 12

Preparation of the compound of the formula (IV)

18.52 g (0.1 mole) of the compound of the formula (III) are dissolved in an aqueous solution of 200 ml of 90% tetrahydrofuran to which at 32°–35° C. 35.59 g (0.2 mole) N-bromo-succinimide and 100 ml of 90% tetrahydrofuran solution are added dropwise. The mixture is further reacted at room temperature for 7 hours and then it is evaporated. Upon cooling a yellow crystalline substance is precipitating which is dissolved hot in carbon-tetrachloride and the undissolved succinimide is filtered off and the filtrate is evaporated. A slowly crystallizing yellow oil is obtained.

Yield: 26.8 g (95%).
Mp.: 128.5°–129.5° C. (literature mp.: 128°–128.5° C., [J. M. Evans et al.: J. Med. Chem. 26, 1582 (1983)].

EXAMPLE 13

Preparation of the compound of the formula (VI)

60 ml of 2-pyrrolidone are heated to 70° C. and under inert atmosphere 2.53 g (0.11 atom) metal-sodium are added. After the addition is completed the solution is cooled to room temperature and 20.12 g (0.1 mole) of the compound of the formula (V) are added and the reaction is continued for 4 hours. The reaction mixture is then poured on 200 g of ice and stirred vigorously. A greyish white precipitate is obtained which is filtered, washed with iced water and dried. The row product is recrystallized from a 3:2 mixture of chloroform and carbon-tetrachloride.

A white crystallite substance is obtained in the form of small needles.

Yield: 25.7 g (90%)
Mp.: 229°–230° C. [literature m.p.: 230°–231° C., V. A. Ashwood et al.: J. Med. Chem. 29, 2194 (1986)].

EXAMPLE 14

Preparation of the end-product of the formula (VI)

60 ml of pyrrolidone are heated to 40° C. and in inert atmosphere 4.30 g (0.11 atom) metal-potassium are added. After the addition is completed, the solution is cooled to room-temperature and 20.12 g (0.1 mole) of a compound of the formula (V) are added and stirred for 4 hours. The reaction mixture is then poured on 200 g of ice and stirred vigorously. A greyish white precipitate is obtained. One may further proceed as given in example 13 and white crystalline substance is obtained in the form of small needles.

Yield: 27.2 g (95%)
Mp.: 229°–230° C.

EXAMPLE 15

Preparation of the end-product of the formula (VI)

90 ml of 2-pyrrolidone are heated to 70° C. and under inert atmosphere 4.83 g (0.21 atom) of metal sodium are added. After the addition is completed the solution is cooled to room temperature and 28.21 g (0.1 mole) of the compound of the formula (IV) are added. After 4 hours of reaction time the reaction mixture is poured on 200 g of ice and stirred vigorously. One may further proceed as given in example 13.

White crystalline substance is obtained in the form of small needles. Yield: 27 g (94%), melting point: 229°–230° C.

EXAMPLE 16

Preparation of the compound of the formula (VI)

20.12 g (0.1 mole) of the compound of the formula (V) are dissolved in 60 ml of 2-pyrrolidone at room temperature and 12.35 g (0.11 mole) of potassium tert-butylate are added. The reaction mixture is maintained at room temperature for 1.5 hours, whereafter it is poured on 200 g of ice. After a while, a pale yellow precipitate is obtained. One may further proceed as given in example 13. White crystalline substance is obtained in the form of small needles.

Yield: 25.5 g (85%)
Mp.: 230°–231° C.

EXAMPLE 17

Preparation of the compound of the formula (VI)

28.21 g (0.1 mole) of the compound of the formula (IV) are dissolved in 90 ml of 2-pyrrolidone at room temperature and under cooling with ice water 23.56 g (0.21 mole) of potassium-tert-butylate are added. When the addition is completed, the mixture is stirred for 1.5 hours at room temperature and poured on 200 g of ice. Pale yellow precipitate is obtained. One may further proceed as given in example 13.

White crystalline substance is obtained in the form of small needles.

Yield: 26 g (91%)
Mp.: 230°–231° C.

What is claimed is:

1. A process for preparing a compound of the Formula (VI)

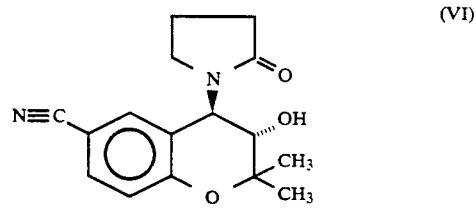

which comprises the steps of:
(a) reacting 4-cyanophenol with isoprene at 30° to 120° C. in a water-immiscible solvent in the presence of an alkali metal and a metal chloride Lewis acid catalyst to yield a compound of the Formula (II)

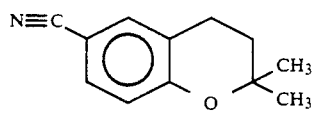

(b) brominating the compound of the Formula (II) with N-bromosuccinimide in a haloalkane solvent in the presence of a trace of peroxide to yield a compound of the Formula (X)

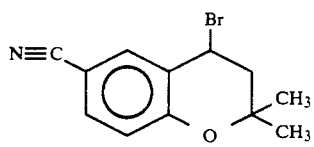

(c) dehydrobrominating the compound of the Formula (X) with an alkali alcoholate to yield a compound of the Formula (III)

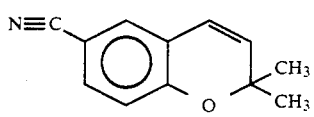

(d) reacting the compound of the Formula (III) with N-bromo-succinimide in tetrahydrofuran at 20° to 120° C. to produce a compound of the Formula (IV)

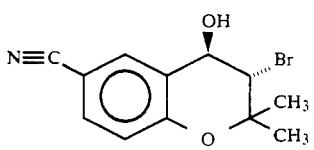

and (e) reacting the compound of the Formula (IV) with 2-pyrrolidone in the presence of an alkali metal or an alkali metal alcoholate at 20° to 100° C. to obtain the compound of the Formula (VI).

2. The process defined in claim 1 wherein according to step (a) the metal chloride Lewis-acid catalyst is selected from the group consisting of $AlCl_3$, $SnCl_4$, and $FeCl_3$.

3. The process for preparing the compound of the Formula (VI) defined in claim 1 wherein according to step (a) the alkali metal is potassium, the metal chloride Lewis acid catalyst is aluminum trichloride, and the water-immiscible solvent is benzene, and wherein the reaction is carried out at a temperature of 60° to 80° C.

4. The process for preparing the compound of the Formula (VI) defined in claim 3 wherein the molar ratio of the 4-cyano-phenol, the isoprene, the potassium, and the aluminum trichloride is 0.8 to 1.2: 0.9 to 2: 0.1 to 0.7: 0.9 to 3.

5. The process for preparing the compound of the Formula (VI) defined in claim 1 wherein according to step (b) the bromination of the compound of the Formula (II) is carried out with 0.9 to 1.5 equivalents of the N-bromo-succinimide in the presence of dibenzoyl peroxide in a haloalkane at 40° to 100° C., and wherein according to step (c), the dehydrobromination of the compound of the Formula (X) is carried out with 0.7 to 1.5 equivalents of the alkali alcoholate in an aromatic solvent at 75° to 85° C.

6. The process for preparing the compound of the Formula (VI) defined in claim 1 wherein according to step (d) the compound of the Formula (III) is reacted with 1 to 1.2 equivalents of N-bromosuccinimide and performing the reaction in a mixture of tetrahydrofuran and water at 30° to 40° C.

7. The process for preparing the compound of the Formula (VI) defined in claim 1 wherein according to step (e) the compound of the Formula (IV) is reacted with 2-pyrrolidone in the presence of 1 to 1.2 equivalents of an alkali metal or an alkali metal alcoholate at 20° to 30° C.

* * * * *